US008574592B2

(12) United States Patent
Hoffmann et al.

(10) Patent No.: US 8,574,592 B2
(45) Date of Patent: *Nov. 5, 2013

(54) MODIFIED INFLUENZA VIRUS FOR MONITORING AND IMPROVING VACCINE EFFICIENCY

(75) Inventors: Erich Hoffmann, Galveston, TX (US); Aleksandr S. Lipatov, Atlanta, GA (US); Richard J. Webby, Memphis, TN (US); Elena A. Govorkova, Cordova, TN (US); Robert G. Webster, Memphis, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/614,835

(22) Filed: Sep. 13, 2012

(65) Prior Publication Data

US 2013/0017216 A1    Jan. 17, 2013

Related U.S. Application Data

(62) Division of application No. 12/964,491, filed on Dec. 9, 2010, now Pat. No. 8,293,247, which is a division of application No. 11/460,584, filed on Jul. 27, 2006, now Pat. No. 7,871,626.

(60) Provisional application No. 60/705,808, filed on Aug. 4, 2005.

(51) Int. Cl.
| | |
|---|---|
| A61K 39/145 | (2006.01) |
| A61K 39/12 | (2006.01) |
| A61K 39/00 | (2006.01) |
| A01N 63/00 | (2006.01) |
| C12Q 1/70 | (2006.01) |
| C12P 21/06 | (2006.01) |
| C07K 14/00 | (2006.01) |

(52) U.S. Cl.
USPC .................. 424/206.1; 424/205.1; 424/199.1; 424/186.1; 424/185.1; 424/209.1; 424/93.6; 435/5; 435/69.1; 530/350

(58) Field of Classification Search
None
See application file for complete search history.

(56) References Cited

U.S. PATENT DOCUMENTS

| 6,719,979 B2 | 4/2004 | Peeters et al. |
| 6,740,325 B1 | 5/2004 | Arnon et al. |
| 7,871,626 B2 * | 1/2011 | Hoffmann et al. ......... 424/206.1 |
| 2005/0003349 A1 | 1/2005 | Kawaoka |

OTHER PUBLICATIONS

GenBank Accession# ABP51975, hemagglutinin [Influenza A virus (A/Hong Kong/213/2003 (H5N1))], Apr. 21, 2007.*
Both et al., "Hemagglutinin of SWine Influenza Virus: A Single Amino Acid Change Pleiotropically Affects Viral Antigenicity and Replication", Proceedings of the National Academy of Sciences USA, 1983, vol. 80, pp. 6996-7000.
Gambrayan et al., "Receptor specificity of influenza viruses from birds and mammals: New data on involvement of the inner fragments of the carbohydrate chain", Virology, 2005, vol. 334, pp. 276-283.
Genbank Accession: AAT39066, hemagglutinin [Influenza A virus (A/HK/213/03 (H5N1 ))], 2004.
Genbank Accession: ABW90135.1, hemagglutinin [Influenza A virus (A/VietNam/1203/2004(H5N1))], 2007.
Glaser et al., "A Single Amino Acid Substitution in 1918 Influenza Virus Hemagglutinin Changes Receptor Binding Specificity", Journal of Virology, 2005, vol. 79, pp. 11533-11536.
Govorkova et al. "Lethality of Ferrts of H5N1 Influeza Viruses Isolated from Humans and Poultry in 2004", Journal of Virology, 2005, vol. 79, pp. 2191-2198.
Guan et al., "H5N1 influenza: A protean pandemic threat", Proceedings of the National Academy of Sciences USA, 2004, vol. 101, pp. 8156-8161.
Ha et al., "H5 avian and H9 swine influenza virus haemagglutinin structures: possible origin of influenza subtypes", The EMBO Journal , vol. 2, pp. 865-875, 2002.
Haque et al., "Confronting Potential Influenza A (H5N1) Pandemic with Better Vaccines", Emerging Infectious Diseases, 2007, vol. 13, pp. 1512-1518.
Hatta et al., "Molecular Basis for High Virulence of Hong Kong H5N1 Influenza A Viruses", Science, 2001, vol. 293, pp. 1840-1842.
Hien et al., "Avian Influenza A (H5N1) in 10 patients in Vietnam", New England Journal of Medicine, 2004, vol. 350, pp. 1179-1188.
Hoffmann et al., "Role of specific hemagglutinin amino acids in the immunogenicity and protection of H5N1 influenza virus vaccines", Proceedings of the National Academy of Sciences USA, 2005, vol. 102, pp. 12915-12920.
Hoffmann, et al., "A DNA transfection system for generation of influenza A virus from eight plasmids", Proceedings of the National Academy of Sciences USA, 2000, vol. 97, pp. 6108-6113.
Kilbourne, "Genetic dimorphism in influenza viruses: Characterization of stably associated hemagglutinin mutants differing in antigenicity and biological properties", Proc. Natl. Acad. Sci. USA, vol. 75, pp. 6258-6262, 1978.
Lee et al., "Generation of reassortant influenza vaccines by reverse genetics that allows utilizations of a DIVA (Differentiating Infected from Vaccinated Animals) strategy for the control of avian influenza", Vaccine, 2004, vol. 22, pp. 3175-3181.
Lewin,G., "Genes VII", Oxford Univ. Press, 2000, p. 778.
Li et al., "Genesis of a highly pathogenic and potentially pandemic H5N1 influenza virus in eastern Asia", Nature, 2004, vol. 430, pp. 209-213.
Lipatov et al., "Efficacy of H5 Influenza Vaccines Produced by Reverse Genetics in a Lethal Mouse Model", Journal of Infectious Disease, 2005, vol. 191, pp. 1216-1220.
Martin et al., "Studies of the Binding Properties of Influenza Hemagglutinin Receptor-Site Mutants", Virology, 1998, vol. 241, pp. 101-111.
Neumann and Kawaoka, "Host Range Restriction and Pathogenicity in the Context of Influenza Pandemic", Emerging Infectious Diseases, 2006, 12(6), pp. 881-886.

(Continued)

Primary Examiner — Benjamin P Blumel
(74) Attorney, Agent, or Firm — Troutman Sanders LLP

(57) ABSTRACT

The immunogenicity of the influenza virus hemagglutinin (HA) molecule may be increased by substitutions of amino acids in the HA sequence. The substitution of specific HA residues, such as asparagine at position 223 of H5 HA, increase the sensitivity of the hemagglutinin inhibition (HI) assay by altering receptor specificity and/or antibody-antigen binding. HA molecules containing such substitutions will be useful in the development of diagnostic reference viruses and improved influenza vaccines.

20 Claims, 3 Drawing Sheets

(56) References Cited

OTHER PUBLICATIONS

Sanofi-Pasteur, 271/371 Fluzone, 372 Fluzone High-Dose, 390 Fluzone Intradermal, 2011, Vaccine Package Insert, pp. 1-34.

Stephenson et al., "Cross-Reactivity to Highly Pathogenic Avian Influenza H5N1 Viruses after Vaccination with Nonadjuvanted and MF59-Adjuvanted Influenza A/Duck/Singapore/97 (H5N3) Vaccine: A Potential Priming Strategy", Journal of Infectious Diseases, 2005, vol. 191, pp. 1210-1215.

Takahashi et al., "Protective Immunity Afforded by Inactivated H5N1 (NIBRG-14) Vaccine Requires Antibodies against both Hemaaglutinin and Neuraminidase in Mice", The Journal of Infectious Diseases, 2009, vol. 199, pp. 1629-1637.

* cited by examiner

Figure 2.

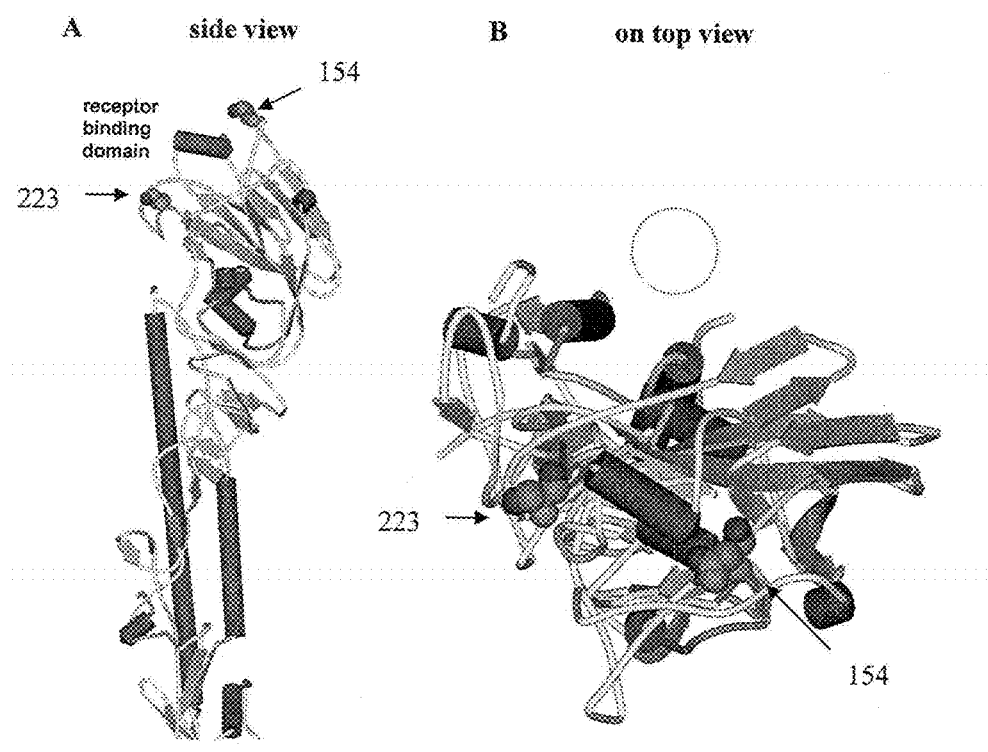

MODIFIED INFLUENZA VIRUS FOR MONITORING AND IMPROVING VACCINE EFFICIENCY

CROSS-REFERENCE TO RELATED APPLICATIONS

This application is a divisional of U.S. application Ser. No. 12/964,491, filed Dec. 9, 2010, which is a divisional of U.S. application Ser. No. 11/460,584, filed Jul. 27, 2006, now U.S. Pat. No. 7,871,626, which claims the benefit of U.S. Provisional Application No. 60/705,808, filed Aug. 4, 2005, all of which are incorporated herein by reference in their entirety.

STATEMENT REGARDING FEDERALLY SPONSORED RESEARCH OR DEVELOPMENT

The research leading to the present invention was supported by grant AI95357 from the National Institute of Allergy and Infectious Disease and by Cancer Center Support (CORE) grant CA21765 from the National Institutes of Health. Accordingly, the U.S. government has certain rights in the invention.

REFERENCE TO A COMPACT DISK APPENDIX

Not applicable.

FIELD OF THE INVENTION

In a general sense, the invention relates to increasing the antigenicity and/or immunogenicity of a group of influenza virus subtypes.

BACKGROUND OF THE INVENTION

Influenza Viruses

Influenza viruses, most notably particular strains of A and B virus, are a serious cause of morbidity and mortality throughout the world, resulting in annual disease outbreaks. Periodically but at irregular intervals pandemics occur and result in particularly high levels of illness and death. Pandemics are historically the result of novel virus subtypes of influenza A, created by reassortment of the segmented genome (antigenic shift), whereas annual epidemics are generally the result of evolution of the surface antigens of influenza A and B virus (antigenic drift). Human influenza viruses often originate from avian strains of influenza virus so that influenza infection is at its basis a zoonosis. There is also evidence that swine can serve as an intermediate host ("mixing vessel") for the generation of new avian-originated strains that are pathogenic in humans (Scholtissek et al., Virology 1985, 147:287). The H5N1 influenza A outbreak in Hong Kong in 1997 showed that highly pathogenic influenza A viruses can also be transmitted directly from avian species to humans (Claas et al., Lancet 1998, 351:472; Suarez et al., J. Virol. 1998, 72:6678; Subbarao et al., Science 1998, 279:393; Shortridge, Vaccine 1999, 17 (Suppl. 1): S26-S29). In 2003, the H5N1 viruses in Southeast Asia comprised different co-circulating genotypes, but in 2004 a single genotype, known as the "Z-genotype", became dominant (Li et al., Nature 2004, 430: 209). Current evidence indicates that fatal human cases resulted from the direct transmission of this genotype from birds to humans and that it also infected cats, with direct cat to cat transmission (Kuiken et al., Science 2004, 306:241). This and other evidence of the changing host range and widespread distribution of this virus raised concern that H5N1 viruses may acquire the characteristics that allow transmission from human to human. Humans would have no immunity to such new H5N1 viruses, which could cause catastrophic pandemic influenza (Fouchier et al., Nature 2005, 435:419). The potential of influenza A viruses to generate new pathogenic strains from a vast number of circulating strains in animal reservoirs indicates that disease control requires monitoring these viruses and developing improved antiviral therapies and vaccines. The speed with which new viral strains develop demands vigilance in this monitoring effort, including improved techniques for assessing the efficacy of vaccines to novel strains.

Influenza A, B and C, of the family Orthomyxoviridae, all have a segmented negative strand RNA genome that is replicated in the nucleus of the infected cell, has a combined coding capacity of about 13 kb, and contains the genetic information for ten viral proteins. Specifically, influenza viruses have eight negative-sense RNA (nsRNA) gene segments that encode at least 10 polypeptides, including RNA-directed RNA polymerase proteins (PB2, PB1 and PA), nucleoprotein (NP), neuraminidase (NA), hemagglutinin (HA, which after enzymatic cleavage is made up of the association of subunits HA1 and HA2), the matrix proteins (M1 and M2) and the non-structural proteins (NS1 and NS2) (Krug et al., In The Influenza Viruses, R. M. Krug, ed., Plenum Press, New York, 1989, pp. 89-152).

Recently developed reverse-genetics systems have allowed the manipulation of the influenza viral genome (Palese et al., Proc. Natl. Acad. Sci. USA 1996, 93:11354; Neumann and Kawaoka, Adv. Virus Res. 1999, 53:265; Neumann et al., Proc. Natl. Acad. Sci. USA 1999, 96:9345; Fodor et al., J. Virol. 1999, 73:9679). For example, it has been demonstrated that the plasmid-driven expression of eight influenza nsRNAs from a pol I promoter and the coexpression of the polymerase complex proteins result in the formation of infectious influenza A virus (Hoffmann et al., Proc. Natl. Acad. Sci. USA 2000, 97:6108).

The virus particle of the influenza virus has a size of about 125 nm and consists of a core of negative sense viral RNA associated with the nucleoprotein, surrounded by a viral envelope with a lipid bilayer structure. The inner layer of the viral envelope is composed predominantly of matrix proteins and the outer layer contains most of the host-derived lipid material. The so-called "surface proteins", neuraminidase (NA) and hemagglutinin (HA), appear as spikes on the surface of the viral body. Infectivity of novel influenza viruses depends on the cleavage of HA by specific host proteases, whereas NA is involved in the release of progeny virions from the cell surface and prevents clumping of newly formed virus.

The HA and NA proteins embedded in the viral envelope are the primary antigenic determinants of the influenza virus (Air et al., Structure, Function, and Genetics, 1989, 6:341-356; Wharton et al., In The Influenza Viruses, R. M. Krug, ed., Plenum Press, New York, 1989, pp. 153-174). Due to reassortment of influenza segmented genome, new HA and NA variants are constantly created for which a newly infected organism has no anamnestic immune response. HA glycoprotein is the major antigen for neutralizing antibodies and is involved in the binding of virus particles to receptors on host cells.

HA molecules from different virus strains show significant sequence similarity at both the nucleic acid and amino acid levels. This level of similarity varies when strains of different subtypes are compared, with some strains clearly displaying higher levels of similarity than others (Air, Proc. Natl. Acad. Sci. USA, 1981, 78:7643). The levels of amino acid similarity vary between virus strains of one subtype and virus strains of other subtypes (Air, Proc. Natl. Acad. Sci. USA, 1981, 78:7643). This variation is sufficient to establish discrete subtypes and the evolutionary lineage of the different strains, but the DNA and amino acid sequences of different strains are still readily aligned using conventional bioinformatics techniques (Air, Proc. Natl. Acad. Sci. USA, 1981, 78:7643; Suzuki and Nei, Mol. Biol. Evol. 2002, 19:501).

Influenza Vaccines

The influenza vaccines currently licensed by public health authorities for use in the United States and Europe are inactivated influenza vaccines as well as the live attenuated FLU-MIST vaccine in the United States. Viruses presenting epidemiologically important influenza A and influenza B strains are grown in embryonated chicken eggs and the virus particles are subsequently purified and inactivated by chemical means to form vaccine stocks. Each year the WHO selects subtypes which most likely will circulate for that year for vaccine development.

Although influenza vaccines have been in use since the early 1940's for human vaccination and since the late 1960's for equine vaccination, the existence of extensive animal reservoirs, combined with the threat of emergence of a novel influenza virus capable of causing a pandemic, has spurred research into novel therapies with which to fight the virus. Several important advances in the field of influenza have occurred in the last few years (reviewed in Cox and Subbarao, Lancet 1999, 354:1277-82). For example, an experimental live, attenuated, intranasally administered trivalent influenza vaccine was shown to be highly effective in protecting young children against influenza A H3N2 and influenza B. Other approaches to improve the efficacy of the current (killed) influenza virus vaccines include the generation of cold-adapted and genetically engineered influenza viruses containing specific attenuating mutations (reviewed in Palese et al., J. Infect. Dis., 1997, 176 Suppl 1:S45-9). It is hoped that these genetically altered viruses, in which the HA and NA genes from circulating strains have been incorporated by reassortment, can be used as safe live influenza virus vaccines to induce a long-lasting protective immune response in humans. Although cold-adapted vaccines appear to be efficacious in children and young adults, they may be too attenuated to stimulate an ideal immune response in elderly people, the major group of the 20000-40000 individuals in the USA dying each year as a result of influenza infection.

Readily available vaccines would provide the most effective tool against emergent pandemic influenza. After the 1997 H5N1 outbreak in Hong Kong, vaccines produced by two different approaches were tested in humans. Conventional subunit H5 vaccine produced from A/duck/Singapore/3/97 was poorly immunogenic in humans, even against antigenically closely related strains and after multiple vaccination (Nicholson et al., Lancet 2001, 357:1937; Stephenson et al., Journal of Infectious Disease 2005, 191:1210). The use of the adjuvant MF59 increased the antibody titer of this H5 vaccine (Stephenson et al., Vaccine 2003, 21:1687). Vaccination with inactivated "split" vaccine derived from nonpathogenic A/duck/HK/836/80 (H3N1) virus and the modified H5 hemagglutinin from A/HK/156/97 (H5N1) virus induced barely detectable titers of neutralizing antibodies (Takada et al., Journal of Virology 1999, 73:8303). Thus, although these H5N1 vaccines were well tolerated, they appeared to be poorly immunogenic. The current lack of effective vaccines against H5N1 virus strains increases the threat of these viruses to cause pandemic disease.

Influenza Vaccine Immunogenicity

Serum antibody titer methods are the accepted surrogate measures of immune protection after vaccination or viral infection. The predominantly used serum antibody titer methods are virus neutralization titer assays and hemagglutinin inhibition (HI) titer assays. These assays are based on the ability of influenza antibodies from human serum to cross react with antigens under in vitro conditions. Assays are selected for a given situation based not only on their ability to provide consistent and applicable results but also based on their ease of use and the facility requirements for each type of assay.

Briefly stated, the virus neutralization assay examines the ability of antibodies from a serum sample to block the infection of cultured cells by influenza virus. The assay is carried out by creating serial dilutions (titers) of a serum sample and combining each of these dilutions with a standard amount of infectious virus. Each dilution mixture is then presented to a defined cell culture and the resulting infection rates assayed. The virus neutralization titer assay is considered to be an extremely useful and reliable test to examine the level of immunoprotective antibodies present in a given individual. It is, however, dependent on specialized cell culture facilities and therefore is not universally available. The methodology is also laborious and time consuming hence poorly suited to screening large numbers of samples.

The hemagglutinin inhibition (HI) assay similarly examines the ability of antibodies from a serum sample to bind with a standardized reference virus. The basis for this assay is the fact that influenza viruses will bind to and agglutinate erythrocytes. In the HI assay, serial dilutions of serum sample are mixed with standard amounts of reference virus and after a set incubation period added to erythrocytes. The association between reference viruses and erythrocytes into complexes is then detected visually. The highest dilution of serum that inhibits hemagglutinin is read as the hemagglutinin inhibition titer. Although not as sensitive of vaccine immunogenicity as other assays, the HI assay is widely employed due to its relatively simple technology and laboratory requirements.

Given the limitations discussed above on the current techniques available for influenza vaccine development and assessment, there is a need for improvements in techniques of immunogenicity assessment to test immune response after infection as well as vaccine efficacy.

SUMMARY OF THE INVENTION

The present invention provides for amino acid substitutions in the hemagglutinin (HA) molecule of influenza A that can alter the antigenicity and immunogenicity of the HA. These substitutions may alter antigenic sites by altering receptor specificity and/or antibody-antigen binding. In a variety of embodiments, the increased antigenicity resulting from the substitution may be useful to increase the sensitivity of the hemagglutinin (HI) assay on serum taken from infected animals. This information is important in the production of diagnostic reference viruses and new vaccines for influenza. Preferably, the amino acid substitution results in molecules with the immunogenicity characteristics of the amino acid substitution of asparagine at H5 HA location 223.

Thus, within certain aspects, the present invention includes an influenza virus hemagglutinin (HA) molecule comprising one or more amino acid substitution in the receptor binding site that makes the HA molecule more antigenic with respect to antibodies specific for the HA molecule lacking the amino acid substitution in its receptor binding site. The influenza virus increased antigenicity HA molecule may include the amino acid asparagine at the position corresponding to position 223 in H5 HA, wherein the inclusion of asparagine results in an increased reactivity with antisera derived from an animal exposed to an influenza virus with a wildtype HA molecule. The influenza virus increased antigenicity HA molecule may include the amino acid asparagine at the position corresponding to position 223 in H5 HA, wherein the HA molecule does not originate with human H5 isolate A/HK/213/03 and the inclusion of asparagine at position 223 results in an increased reactivity with antisera derived from an animal exposed to an influenza virus. In some embodiments, the amino acid substitution alters a glycosylation site. In some embodiments, the influenza virus is a human influenza A virus. For example, the human influenza A virus may be a member of the H5 subtype. The human influenza A virus may be a A/Vietnam/1203/04 (H5N1) virus. In some embodiments, the influenza virus is an influenza B virus. The invention includes influenza virus increased antigenicity HA molecules that are derived from an avian influenza virus.

Within other aspects, the invention includes a recombinant influenza virus comprising an influenza virus hemagglutinin (HA) molecule comprising one or more amino acid substitution in the receptor binding site that makes the HA molecule more antigenic with respect to antibodies specific for the HA molecule lacking the amino acid substitution in its receptor binding site. The recombinant virus may include a modified HA molecule derived from H5N1 influenza virus in the genetic background of an influenza A virus. The influenza A virus may be a master strain virus. The recombinant virus may be used as a diagnostic reference virus in a hemagglutinin inhibition (HI) assay. The recombinant influenza virus may be included in a hemagglutinin inhibition (HI) assay kit.

Still further aspects of the invention include reverse genetics systems for making a virus containing an influenza virus hemagglutinin (HA) molecule comprising an amino acid substitution in the receptor binding site that makes the HA molecule more antigenic with respect to antibodies specific for the HA molecule lacking the amino acid substitution in its receptor binding site.

Yet other aspects of the invention disclosed herein include methods of making a virus containing an influenza virus hemagglutinin (HA) molecule comprising one or more amino acid substitution in the receptor binding site that makes the HA molecule more antigenic with respect to antibodies specific for the HA molecule lacking the amino acid substitution in its receptor binding site. In some embodiments, the method comprises introducing a recombinant vector that expresses the increased antigenicity HA molecule in a reverse genetics system.

In related aspects, the invention further provides methods for determining the efficacy of an influenza virus vaccine in an animal. In some embodiments, the method comprises reacting antisera derived from a vaccinated animal with an influenza virus hemagglutinin (HA) molecule comprising one or more amino acid substitution in the receptor binding site that makes the HA molecule more antigenic with respect to antibodies specific for the HA molecule lacking the amino acid substitution in the receptor binding site which is present in the influenza virus vaccine. In some embodiments, the increased antigenicity HA molecule originates with human H5N1 isolate A/HK/213/03 and the inclusion of asparagine at the position that corresponds to position 223 in HA from H5N1 virus results in an increased reactivity with antisera derived from the vaccinated animal. In some embodiments, the animal is a human. In other embodiments, the animal is a ferret.

Yet other related aspects of the present invention provide methods for producing an influenza virus comprising a hemagglutinin (HA) molecule, which method comprises culturing a reverse genetics system in which DNA encoding HA encodes one or more amino acid substitution in the receptor binding site that makes the HA molecule more antigenic with respect to antibodies specific for the HA molecule lacking the amino acid substitution in the receptor binding site by a reverse genetics process.

The invention further provides methods for increasing the sensitivity of a hemagglutinin inhibition (HI) assay, which methods comprise reacting antisera derived from the vaccinated or infected animal with an influenza virus hemagglutinin (HA) molecule comprising one or more amino acid substitution in the receptor binding site that makes the HA molecule more antigenic with respect to antibodies specific for the HA molecule lacking the amino acid substitution in the receptor binding site. In some embodiments, the method for increasing the sensitivity of a HI assay results in at least 2-fold increase in sensitivity of a hemagglutinin inhibition (HI) assay. In some embodiments, the method for increasing the sensitivity of a HI assay results in at least 4-fold increase in sensitivity of a hemagglutinin inhibition (HI) assay.

Another aspect of the invention includes methods for determining whether an animal has been exposed to an influenza virus. In some embodiments, the method comprises reacting antisera derived from the animal with a diagnostic reference virus, which is derived from the influenza virus in question but comprises an influenza virus hemagglutinin (HA) molecule comprising an amino acid substitution in the receptor binding site that makes the HA molecule more antigenic with respect to antibodies specific for the HA molecule lacking the amino acid substitution in its receptor binding site resulting in an increased reactivity with the antisera. In some embodiments, the animal is a human. In other embodiments, the animal is a ferret.

The invention includes in yet other aspects methods for determining whether an animal has been exposed to an influenza virus. In some embodiments, the method comprises reacting antisera derived from the animal with a diagnostic reference virus, which is derived from the influenza virus in question but comprises a modified influenza virus HA molecule comprising the amino acid asparagine at the position corresponding to position 223 in H5 HA, wherein the inclusion of asparagine results in an increased reactivity with antisera derived from an animal exposed to an influenza virus with a wildtype HA molecule, resulting in an increased reactivity with the antisera. In some embodiments, the method for determining whether an animal has been exposed to an influenza virus includes reacting antisera derived from the animal with a diagnostic reference virus, which is derived from the influenza virus in question but comprises a modified influenza virus HA molecule comprising the amino acid asparagine at the position corresponding to position 223 in H5 HA, wherein the HA molecule does not originate with human H5 isolate A/HK/213/03 and the inclusion of asparagine at position 223 results in an increased reactivity with antisera derived from an animal exposed to an influenza virus. In some embodiments, the animal is a human. In other embodiments, the animal is a ferret.

Also included within the invention are influenza vaccine viruses comprising a hemagglutinin (HA) molecule comprising an amino acid substitution in the receptor binding site that makes the HA molecule more antigenic with respect to antibodies specific for the HA molecule lacking the amino acid substitution in the receptor binding site and wherein the modification results in an increased immunogenicity of said vaccine virus.

One aspect of this invention includes isolated nucleic acids encoding an influenza virus hemagglutinin (HA) molecule comprising an amino acid substitution in the receptor binding site that makes the HA molecule more antigenic with respect to antibodies specific for the HA molecule lacking the amino acid substitution in its receptor binding site. In some embodiments, the influenza virus HA molecule encoded by the isolated nucleic acid comprises an amino acid asparagine at the position corresponding to position 223 in H5 HA, wherein the HA molecule does not originate with human H5 isolate A/HK/213/03 and the inclusion of asparagine at position 223 results in an increased reactivity with antisera derived from an animal exposed to an influenza virus.

The invention further includes methods for preparing nucleic acids encoding an influenza virus hemagglutinin (HA) molecule comprising an amino acid substitution in the receptor binding site that makes the HA molecule more antigenic with respect to antibodies specific for the HA molecule lacking the amino acid substitution in its receptor binding site. In some embodiments, the method comprises introducing a nucleotide sequence into a nucleic acid encoding the HA molecule lacking the amino acid substitution in the receptor binding site, which results in an amino acid substitution in the sequence of the HA molecule that makes the HA molecule more antigenic with respect to antibodies for the HA molecule lacking the amino acid substitution.

The present invention meets these and other aspects of the invention, as set forth in greater detail in the Detailed Description and Examples.

DESCRIPTION OF THE DRAWINGS

In FIG. 1A, sera were collected on day 28 after inoculation with $10^6$ $EID_{50}$ of H5N1 viruses and titrated against 4 hemagglutinating units (HAU) of homologous virus. Data are representative values from two or 4 sera. In FIG. 1B, sera were collected from ferrets vaccinated×2 with 7 μg HA of ΔH5N1/03 and ΔH5N1/04 viruses and titrated against 4 HAU and 100 $TCID_{50}$ of homologous virus, respectively.

FIG. 2 is a graph indicating virus titers in nasal washes of vaccinated and control ferrets after challenge with A/Vietnam/1203/04 (H5N1) virus. Ferrets vaccinated with ΔH5N1/04 or ΔH5/04 recombinant viruses were inoculated intranasally with $10^6$ $EID_{50}$ of A/Vietnam/1203/04 virus. Titers are the mean values ($\log_{10}$ $EID_{50}$/0.1 ml)±SD determined in the nasal washes of 3 ferrets.

Figure 1:
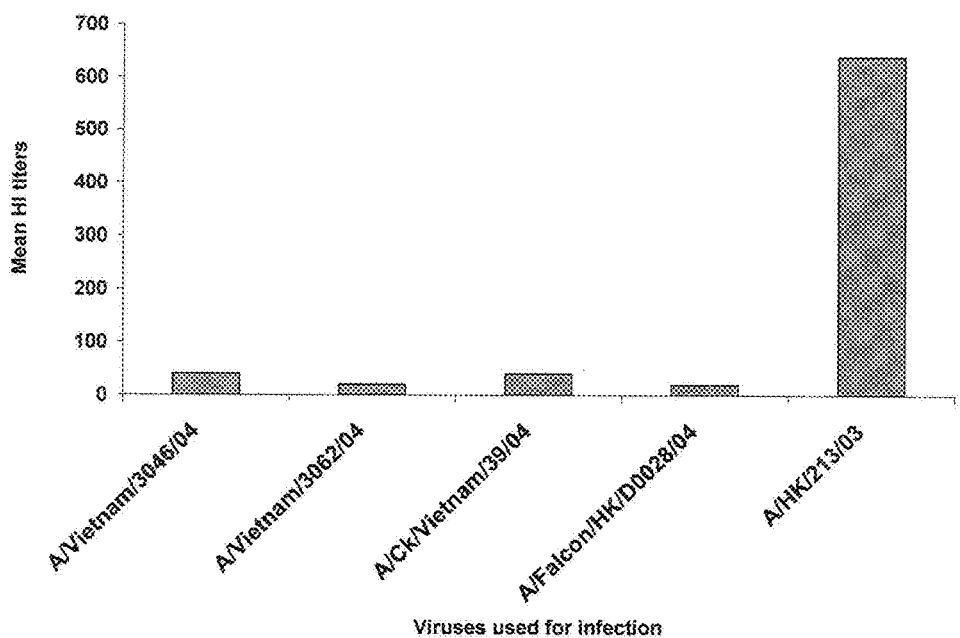
FIG. 1 is a graph indicating HI antibody titers in ferrets inoculated with H5N1 influenza viruses isolated in 2003 and 2004 (A); HI and virus neutralizing titers in ferrets immunized with ΔH5N1/03 and ΔH5N1/04 viruses (B).
Figure 1:
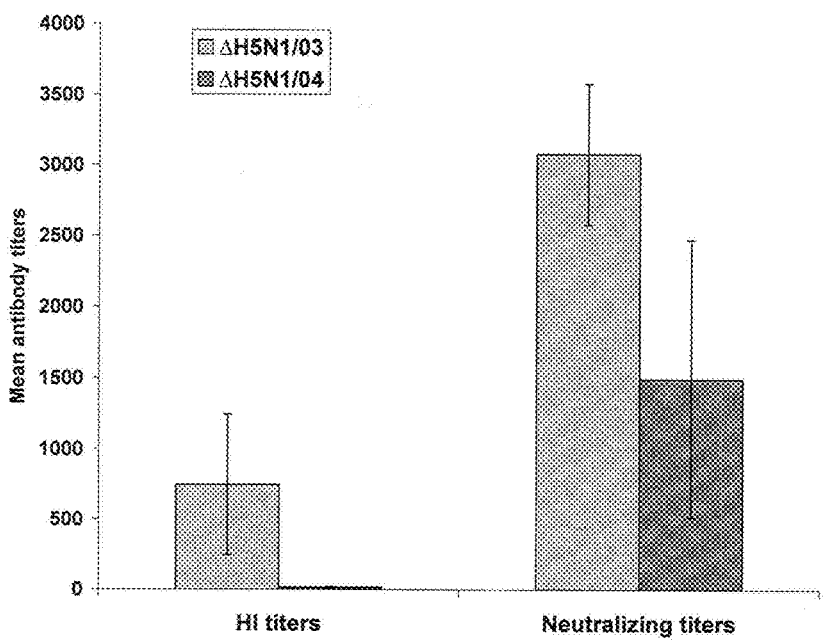

Note that differences in titers between vaccinated and control groups are significant at P values 0.0028-0.0173 according to unpaired t test results.

FIG. 3 is a molecular model of the H5 HA polypeptide showing the location of amino acid at positions 154 and 223 in the 3D structure of the HA of A/duck/Singapore/3/97 (H5N3) virus. In FIG. 3A, the receptor binding site of the amino acids in the 3D structure are indicated. In FIG. 3B, the circle represents the interface between the monomer shown and two other monomers (not shown) in the trimeric HA. The amino acid at position 223 is located in the 220-loop of the receptor binding domain between the glutamine generally present at location 222 and the glycine generally present at location 224.

DETAILED DESCRIPTION

The present invention provides for amino acid sequence changes of the hemagglutinin (HA) molecule of influenza virus, which make the HA molecule more antigenic with respect to antibodies specific for HA molecules lacking the changes. Such sequence changes include substitutions and deletions. The resulting HA is referred to as an "increased antigenicity HA."

The increased antigenicity HA molecule is useful in testing vaccine efficacy, as the change increases the sensitivity of diagnostic tests for antibodies against influenza virus in serum. In a specific embodiment the virus is an influenza A virus. In an alternate embodiment, the virus can also be an influenza B virus, and in still another embodiment it can be an influenza C virus. In an embodiment in which the influenza is an influenza A virus, it can be a H5-subtype influenza A virus. In a more specific embodiment, the H5-subtype HA molecule is modified to include the amino acid asparagine at position 223 ($N_{223}$), resulting in an increased reactivity with antisera derived from an animal exposed to a H5-subtype influenza virus. In a specific embodiment the HA molecule of the invention is not an A/HK/213/03 HA molecule, which is a naturally occurring H5-subtype with asparagine at position 223. The influenza virus may be a human influenza A virus of the H5 subtype, including A/Vietnam/1203/04 (H5N1) virus.

An amino acid changes that makes the HA molecule more antigenic can be made in the reception binding domain of HA, e.g., as depicted in FIG. 3A, particularly in the 220-loop region in the receptor binding domain. Such a change may reduce HA binding to sialic acid receptors on red blood cells, thus increasing the ability of anti-HA antibodies to inhibit hemagglutination, resulting in amplification of the effect of antibody binding activity in a hemagglutination inhibition assay. Alternatively, an amino acid change that makes the HA molecule more antigenic can be made to alter or delete a glycosylation site on the HA protein, particularly a glycosylation site that masks epitopes on HA recognized by HA-specific antibodies. In still another embodiment, the amino acid change can be made to an amino acid residue corresponding to residue 223 of the H5 HA subtype. In all of the embodiments of the invention, amino acid modifications that make an HA molecule more antigenic can be readily identified by immunoassays using antibodies specific for the particular HA subtype. A modification that makes the HA molecule more antigenic will result in apparent higher titer antibody binding activity, relative to the binding activity with the HA molecule to which the antibodies were elicited. Such assays include hemagglutinin inhibition (HI) assays.

In a specific embodiment, substitution in an H5-subtype HA molecule of a serine residue (which may be a glycosylated residue) with asparagine (which is either not glycosylated or differently glycosylated) results in increase antigenicity. However, other substitutions can also result in an apparent increased antigenicity. Such substitutions may be, but need not be, conservative, such as threonine for serine, or glutamine for asparagine. They may preserve the relative polarity, such as asparagine for serine, or lysine for aspartic acid, which conserves polarity without maintaining the same change. It is also contemplated to substitute with residues such as glycine and alanine that eliminate a reactive side chain without having a lot of effect on the polypeptide structure. Finally, completely non-conservative changes are possible. Again, simple immunoassays will indicate whether a particular change results in increased antigenicity.

Some avian H5N1 viruses isolated in Central and South America have a basic amino acid, arginine, at position 223. The neutral amino acid asparagine at location 223 is found in the HA of the human isolate A/HK/213/03. This amino acid residue is located in the 220-loop of the receptor binding domain between the glutamine generally present at location 222 and the glycine generally present at location 224 (FIG. 3). The experimental evidence suggests that the higher HI titers reflect a change in receptor specificity. Indeed, the glutamine generally present at location 222 and the glycine generally present at location 224 bind directly to the sialic acid receptor. Amino acids in the 220 loop or adjacent to it are important for the conformation of the receptor binding pocket (Ha et al., Proc. Natl. Acad. Sci. USA 2001, 98:11181). Although the present invention does not rely on any particular explanation of the observed effect, it is possible that substitution of asparagine for serine at position 223 of H5 results in conformational changes and altered receptor specificity.

In a further aspect, HA molecules modified in accordance with the invention to be more antigenic are also more immunogenic. Such molecules can elicit a stronger or more potent immune response as a component of an influenza vaccine, which in turn results in greater protection against influenza infection.

Influenza viruses originating from avian reservoirs are of particular concern to public health. These viruses are believed to be particularly likely to cause pandemic influenza outbreaks in humans. A HA molecule from an avian subtype with increased antigenicity and/or immunogenicity would therefore be particularly useful in immunoassays conducted in conjunction with vaccine development. The strategy exemplified herein with respect to H5 is useful in increasing HI (hemagglutinin inhibition) assay titers against other HA subtypes, and this is particularly useful for evaluating immunity to avian influenza. In some embodiments, the HA molecule with the amino acid substitution in the receptor binding site may be derived from an avian influenza virus, including subtypes H1 through H16 inclusively.

One aspect of this invention includes the use of recombinant influenza virus that has an increased antigenicity HA molecule as a reference virus in an immunoassay, in particular a HI assay, including a kit for performing such an assay. For example, the amino acid substitution of asparagine at position 223 in the H5 HA molecule increases binding to red blood cell (RBC) sialic acid receptors with alpha 2,6 linkage, such as those from chickens, but decreased binding to receptors with a N-glycosyl sialic acid alpha 2,3 linkage, such as those from horse. Thus one aspect of the invention provides that the resultant lower binding on horse RBCs would require a smaller quantity of antibody to inhibit hemagglutination. This concept, of introducing amino acid substitutions that increase antigenicity, as measured by antibody binding, can be applied to all 16 HA subtypes, including those from avian influenza A viruses.

The invention includes methods for determining the efficacy of an influenza virus vaccine in an animal. This method involves reacting antisera derived from the vaccinated animal with an influenza virus that has increased antigenicity hemagglutinin (HA) molecule. Some aspects of methods for determining the efficacy of an influenza virus vaccine in an animal, as demonstrated in the examples, include reacting antisera derived from the vaccinated animal with an influenza virus H5-subtype HA molecule containing the amino acid asparagine at position 223 ($N_{223}$), e.g., the HA molecule from human H5N1 isolate A/HK/213/03. Asparagine at position 223 results in an increased reactivity with antisera derived from an animal exposed to a different H5 influenza virus. The vaccinated animal may be any one of a number of species, including ferrets and humans.

Also included within this invention are methods for increasing the sensitivity of a HI assay by using a reference virus which includes an increased antigenicity HA molecule. In some embodiments, such as when HA molecule originates with a human H5N1 isolate of the A/HK/213/03 strain, the amino acid change is the presence of an asparagine at position 223, resulting in an increased reactivity with antisera derived from an animal exposed to an H5 influenza virus with a different amino acid residue at that position, such as A/Vietnam/1203/04. This increased reactivity may be of any level, including at least a 2-fold or at least a 4-fold increase in reactivity. A 2-fold or 4-fold increase in sensitivity could be especially significant in situations in which the endpoints of conventional titration methods are below the limit of detection.

In a specific embodiment, the invention also includes using as a diagnostic reference virus a recombinant influenza virus that includes a modified H5-subtype HA molecule with the amino acid asparagine at position 223, resulting in an increased reactivity with antisera derived from an animal exposed to a H5 influenza virus. In a specific embodiment, the H5 HA molecule in the diagnostic reference virus originates with a human H5N1 isolate of strain A/HK/213/03. In another embodiment, an asparagine (or glutamane) is substituted in position 223 of an H5 molecule from another influenza strain. It is readily apparent that the same approach can be adapted to any HA molecule from any influenza strain. In various embodiments, the animal may be of a number of species, including ferrets and humans.

In addition to the use of reference viruses with increased sensitivity in human vaccine clinical trials, these viruses can be used in seroepidemiology studies. The availability of data showing how many humans were infected with H5N1 viruses by rapid and simple detection methods like HI assays provides important information on the prevalence of H5N1 viruses in humans. This data can be used to assess the probability of H5N1 viruses spread from human-to human or between avian species and humans.

Other aspects of the invention include methods for determining whether an animal has been exposed to an influenza virus by reacting antisera derived from the animal with a diagnostic reference virus. The diagnostic reference virus is derived from the same strain of influenza virus as the exposure virus, but the reference virus contains an increased antigenicity HA molecule. In one embodiment, the reference virus comprises an HA molecule with an asparagine at the position corresponding to position 223 in H5 HA, wherein the inclusion of asparagine results in an increased reactivity with antisera derived from an animal exposed to an influenza virus with a wildtype HA molecule, resulting in an increased reactivity with the antisera. In another embodiment, the reference virus comprises an influenza virus hemagglutinin (HA) molecule comprising an amino acid asparagine at the position corresponding to position 223 in H5 HA, and the HA molecule does not originate with human H5 isolate A/HK/213/03 and the inclusion of asparagine at position 223 results in an increased reactivity with antisera derived from an animal exposed to an influenza virus. In a specific embodiment, the contracted virus is an H5N1 virus and the reference virus is human H5N1 isolate A/HK/213/03, which includes asparagine at amino acid position 223, resulting in an increased reactivity with the H5N1-specific antisera. In different aspects of the invention, the animal may be of any species, including ferrets and humans.

The invention also encompasses influenza vaccines including an increased antigenicity HA molecule. In a specific embodiment, the virus is a human H5N1 isolate. In a more specific embodiment, the HA is derived from A/HK/213/03. In still another embodiment, the HA is an H5 modified to include the amino acid asparagine at position 223.

Introducing modifications in the HA molecule requires manipulation at the genetic level, as is well-known in the art, as explained in greater detail below. Once a modified HA gene is prepared, a number of approaches are available, such as "reverse genetics" approaches, for introducing the modified HA molecule into an influenza virus, which can then become an reference virus for testing vaccine efficacy, or a diagnostic reference virus for following influenza epidemics, including animal-human virus spread and human-human virus spread.

In some aspects, the invention includes recombinant influenza viruses comprising an influenza virus hemagglutinin (HA) molecule with at least one amino acid sequence change that makes the HA molecule more antigenic with respect to antibodies specific for HA molecules lacking the changes. The amino acid sequence change may include a substitution or deletion of one or more amino acids. The modified HA molecule may be derived from H5N1 influenza virus in the genetic background of an influenza A virus. In some embodiments, the influenza A virus is a master strain virus. The recombinant viruses comprising a modified HA molecule that is more antigenic with respect to antibodies specific for HA molecules lacking the amino acid sequence change may be used as a diagnostic reference virus in a hemagglutinin inhibition (HI) assay. The recombinant virus may also be included in a hemagglutinin inhibition (HI) assay kit.

In other aspects, the invention includes methods of making a virus comprising a hemagglutinin (HA) molecule. For example, one aspect of the invention is a method of making a virus containing an influenza virus hemagglutinin (HA) molecule with at least one amino acid sequence change that makes the HA molecule more antigenic with respect to antibodies specific for HA molecules lacking the changes. The method may include introducing a recombinant vector that expresses modified HA in a reverse genetics system. A method for producing an influenza virus with a hemaglutinin (HA) molecule may include culturing a reverse genetics system in which DNA encoding HA encodes an amino acid substitution in the receptor binding site that makes the HA molecule more antigenic with respect to antibodies specific for the HA molecule lacking the amino acid substitution in the receptor binding site by a reverse genetics process.

Also included in the invention are methods for preparing nucleic acids encoding a hemagglutinin (HA) molecule. The HA molecule may contain at least one amino acid sequence change that makes the HA molecule more antigenic with respect to antibodies specific for HA molecules lacking the changes. In some embodiments, the method comprises introducing a nucleotide sequence into a nucleic acid encoding the HA molecule lacking the amino acid substitution in the receptor binding site, which results in an amino acid substitution in the sequence of the HA molecule that makes the HA molecule more antigenic with respect to antibodies for the HA molecule lacking the amino acid substitution.

DEFINITIONS

The term "influenza virus" is used herein to define a viral species of which pathogenic strains cause the disease known as influenza or flu.

The term "master strain virus" refers to a viral strain is used in the construction of high growth or attenuated vaccine strains. These master strains typically contribute six gene segments to the vaccine virus (PB1, PB2, PA, NP, NA, M and NS). The master strain virus may be a strain that is also in use as a vaccine component, including virus strain A/PR/8/34.

The term "polypeptide" refers to a polymer of amino acids and does not refer to a specific length of the product; thus, peptides, oligopeptides, and proteins are included within the definition of polypeptide. This term also does not refer to, or exclude, post-translational modifications of the polypeptide, for example, glycosylations, acetylations, phosphorylations, and the like.

As used herein, "infectious" refers to the ability of a virus to replicate in a cell and produce viral particles. Infectivity can be evaluated either by detecting virus, i.e., viral load, or by observing disease progression in the animal.

An "individual" or "subject" or "animal", as used herein, refers to vertebrates that support a negative strand RNA virus infection, specifically influenza virus infection, including, but not limited to, birds (such as water fowl and chickens) and members of the mammalian species, such as canine, feline, lupine, mustela, rodent (racine, murine, etc.), equine, bovine, ovine, caprine, porcine species, and primates, the latter including humans. In a specific embodiment, the subject is a ferret, which is a good animal model for studying influenza. In another embodiment, the subject is a human.

As used herein, the term "immunogenic" means that the virus or polypeptide is capable of eliciting a humoral or cellular immune response, and preferably both. An immunogenic entity is also antigenic. An immunogenic composition is a composition that elicits a humoral or cellular immune response, or both, when administered to an animal.

A molecule is "antigenic" when it is capable of specifically interacting with an antigen recognition molecule of the immune system, such as an immunoglobulin (antibody) or T cell antigen receptor. An antigenic polypeptide contains an "epitope" of at least about five, and preferably at least about 10, amino acids. An antigenic portion of a polypeptide, also called herein the "epitope", can be that portion that is immunodominant for antibody or T cell receptor recognition, or it can be a portion used to generate an antibody to the molecule by conjugating the antigenic portion to a carrier polypeptide for immunization. A molecule that is antigenic need not be itself immunogenic, i.e., capable of eliciting an immune response without a carrier.

As used herein, the term "amino acid substitution" refers to the presence of an amino acid at a particular location in the amino acid sequence of that molecule. The amino acid substitution occurs relative to any other amino acid that could have occupied that location. The polypeptide that results from the amino acid sequence change may include changes in post-translational modifications such as glycosylations, acetylations, phosphorylations or any other amino acid modifications as well as the amino acid substitution.

The term "reverse genetics system" as used herein refers to methods of generating influenza virus particles, polypeptides, virons or nucleic acids by genetic engineering methods. These methods include but are not limited to the "plasmid system" as described by Hoffmann (Hoffmann et al., Vaccine 2002, 20:3165; US Patent Publication 2002/0164770A1, 7 Nov. 2002, which is hereby incorporated by reference in its entirety). Generally speaking, reverse genetics systems allow for the creation of virus particles, polypeptides, and/or nucleic acids with specific sequences by genetic engineering methods known to those of skill in the art. These systems are also described in greater detail below.

As used herein the term "receptor binding site" refers to the portion of the HA molecule where the receptor of interest, such as sialic acid receptor on a red blood cell, binds. The structure of the H5 molecule of A/duck/Singapore, and the location of the receptor binding site for hemagglutinin of the H5 subtype, is known and described (Ha et al., Proc. Natl. Acad. Sci. USA 2001 98:11181). The molecular model of this H5 HA, including the receptor binding site, is shown in FIG. 3.

The term "diagnostic reference virus" refers to a virus with enhanced HA antigenicity. Such a diagnostic reference virus can be used in an immunoassay, e.g., the hemagglutinin inhibition assay.

The term "exposure virus" refers to a virus to which an individual animal has been exposed. This exposure can be in the course of daily activities, such as contact with an infected subject, e.g., leading to exposure of a human to an infectious influenza virus. The exposure can also be due to a specific clinical challenge, such as in a laboratory testing situation where a laboratory animal such as a ferret is intentionally exposed to a virus. Such exposure can be expressly generated through immunization with an influenza vaccine.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18$^{th}$ Edition.

As used herein, the term "adjuvant" refers to a compound or mixture that enhances the immune response to an antigen. An adjuvant can serve as a tissue depot that slowly releases the antigen and also as a lymphoid system activator that non-specifically enhances the immune response (Hood, et al., *Immunology, Second Ed.*, Menlo Park, Calif.: Benjamin/Cummings, 1984. p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, and potentially useful human adjuvants such as N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine, BCG (bacille Calmette-Guerin) and *Corynebacterium parvum*. Preferably, the adjuvant is pharmaceutically acceptable.

As used herein, the term "isolated" means that the referenced material is removed from its native environment, e.g., a cell or virus. Thus, an isolated biological material can be free of some or all cellular components, i.e., components of the cells in which the native material occurs naturally (e.g., cytoplasmic or membrane component). A material shall be deemed isolated if it is present in a cell extract or supernatant. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined or proximal to non-coding regions (but may be joined to its native regulatory regions or portions thereof), or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like, i.e., when it forms part of a chimeric recombinant nucleic acid construct. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e., contaminants, including native materials from which the material is obtained. For example, a purified virion is preferably substantially free of host cell or culture components, including tissue culture or egg proteins, non-specific pathogens, and the like. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Methods for purification are well-known in the art. Viral particles can be purified by ultrafiltration or ultracentrifugation, preferably continuous centrifugation (see Furminger, supra). Other purification methods are possible and contemplated herein. A purified material may contain less than about 50%, preferably less than about 75%, and most preferably less than about 90%, of the cellular components, media, proteins, or other nondesirable components or impurities (as context requires), with which it was originally associated. The term "substantially pure" indicates the highest degree of purity which can be achieved using conventional purification techniques known in the art.

In a specific embodiment, the term "about" or "approximately" means within a statistically meaningful range of a value. Such a range can be within an order of magnitude, preferably within 50%, more preferably within 20%, more preferably still within 10%, and even more preferably within 5% of a given value or range. The allowable variation encompassed by the term "about" or "approximately" depends on the particular system under study, and can be readily appreciated by one of ordinary skill in the art.

Hemagglutinin

Hemagglutinin (HA) is the major envelope glycoprotein of influenza A and B viruses. Hemagglutinin-esterase (HE) of influenza C viruses is the HA homologue in these viruses.

New subtypes of HA molecules, typically introduced from aquatic birds, known to be the natural reservoirs of influenza viruses, result in influenza pandemics (see Suzuki and Nei, Mol. Biol. Evol. 2002; 19(4): 501-509).

HA contains two polypeptide chains, HA1 and HA2, encoded by a single gene and derived from proteolysis of a single precursor molecule, including loss of a signal peptide (Suzuki and Nei, supra; Air, Proc. Natl. Acad. Sci. USA 1981; 78(12): 7639-7643). HA 1 has about 320 amino acids, and is receptor-binding protein and the major target of immune responses. HA2 has about 220 amino acids, and provides the anchor to the viral envelope (Suzuki and Nei, supra).

HA genes from influenza A are classified into 16 subtypes, according to their antigenic properties. Influenza B and C virus HA (HE) genes are not classified into subtypes. The sequences of influenza subtypes H1 to H15, and influenza B and C HA (HE) are shown in Suzuki and Nei, supra, FIG. 1, which is incorporated by reference. A comparison of the sequences of influenza A HA subtypes H1, H2, H3, H4, H5, H6, H7, H8, H9, H10, H11, and H12, including conserved amino acids residues from all twelve subtypes are shown in FIG. 1 of Air, supra, which is incorporated by reference. Both references disclose the strains from which these sequences were obtained.

New HA molecules of the invention are created by introducing changes to the amino acid sequence of HA molecule that results in increased antigenicity. Isolation of nucleic acids encoding such HA molecules is routine (see Air, supra), as is modification of the nucleic acid to introduce changes in the amino acid sequence, e.g., by site-directed mutagenesis.

In an alternative embodiment, HA molecules from one strain of a particular HA subtype already contain an amino acid sequence that increases their antigenicity relative to HA molecules of the same subtypes from a different strain, as exemplified herein with respect to A/HK/213/03, relative, e.g., to A/Vietnam/1203/04. In this case, the influenza strain with the more antigenic HA molecule could serve as a diagnostic reference strain. In another embodiment, amino acid residues from the more antigenic HA can be introduced or substituted into the sequence of the less antigenic HA molecule to make it an increased antigenicity HA molecule.

Various changes in the sequence of an HA molecule can result in increased antigenicity. As noted above, the HA1 chain, which is the reception binding domain and major target of immune response is the chain in which such changes can be made. The changes can increase antibody affinity for the HA molecule, e.g., by eliminating a glycosylation site that makes an epitope, or by favoring a conformation with enhanced antibody binding affinity. Alternatively, the change can result in decreased binding to HA receptor, e.g., a sialic acid receptor on a red blood cell, making antibodies specific for the HA molecule more effective competitors for the hemagglutinin reaction. The various immunoassays capable of demonstrating these changes, including the hemagglutinin inhibition (HI) assay, are well-known in the art.

The HI assay involves whole influenza virus particles, as do the current vaccines. Thus, the invention provides for influenza viruses with increased antigenicity HA molecules. Such viruses are most conveniently generated through a "reverse genetics" approach, although it is also possible to use classical reassortment as well.

Reverse Genetics Methods

Recently developed reverse-genetics systems have allowed the manipulation of the influenza viral genome (Palese et al., Proc. Natl. Acad. Sci. USA 1996, 93:11354; Neumann and Kawaoka, Adv. Virus Res. 1999, 53:265; Neumann et al., Proc. Natl. Acad. Sci. USA 1999, 96:9345; Fodor et al., J. Virol. 1999, 73:9679; US Patent Application 20040029251). For example, it has been demonstrated that the plasmid-driven expression of eight influenza vRNAs from a pol I promoter and all mRNAs from a polII promoter result in the formation of infectious influenza A virus (Hoffmann et al., Proc. Natl. Acad. Sci. USA 2000, 97:6108; US Patent Publication No. 20020164770, which is incorporated by reference for its description of a minimal plasmid reverse genetics system, and for its description of genetic engineering methods). These recombinant methods allow for the specific production of influenza virus types with specific alterations to the polypeptide amino acid sequence. A HA molecule containing a desired substitution may be part of a recombinant influenza virus. The recombinant influenza virus may be made by any means known to those of skill in the art, including through a genetic engineering method such as the "plasmid only" system (Hoffmann et al., Vaccine 2002, 20:3165). The recombinant influenza virus may be derived from a H5N1 virus. The recombinant virus may have the genetic background of a H1N1 virus used in vaccine development such as A/PR/8/34 virus or any influenza A virus, including cold-adapted strains of A/Leningrad/134/17/57, A/Leningrad/134/47/57 and A/Ann Arbor/6/60. The nucleic acid corresponding to the HA molecule sequence may be isolated from the virus and sequenced.

Techniques to isolate and modify specific nucleic acids and proteins are well known to those of skill in the art. In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition. Cold Spring Harbor, N.Y.: Cold Spring Harbor Laboratory Press, 1989 (herein "Sambrook et al., 1989"); *DNA Cloning: A Practical Approach*, Volumes I and II (D. N. Glover ed. 1985); Oligonucleotide Synthesis (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); Ausubel, F. M. et al. (eds.). *Current Protocols in Molecular Biology*. John Wiley & Sons, Inc., 1994. These techniques include site directed mutagenesis employing oligonucleotides with altered nucleotides for generating PCR products with mutations (e.g., the "Quikchange" kit manufactured by Stratagene).

Immunoassays

Various means known in the art for detecting immunospecific binding of an antibody to an antigen can be used to detect the binding and increased antigenicity in accordance with the present invention. An early method of detecting interaction between an antigen and an antibody involved detection and analysis of the complex by precipitation in gels. A further method of detecting an analyte-detector antibody binding pair includes the use of radioiodinated detector antibodies or a radioiodinated protein which is reactive with IgG, such as Protein A. These early methods are well known to persons skilled in the art, as reviewed in Methods in Enzymology 1980, 70:166-198.

Later methods for determining the presence of an analyte in a sample using only one antibody include competitive binding assays. In this technique the antibody, which most often would be immobilized onto a solid support, would be exposed to a sample suspected of containing the analyte together with a known quantity of labeled analyte. The two analytes, the labeled analyte and the analyte in the sample, would then compete for binding sites on the antibody. Either free labeled analyte or bound labeled analyte is determined and from this measurement the amount of competing analyte in the sample is known. A more complete description of this method is disclosed in "Basic Principles of Antigen-Antibody Reaction" (Labat, Methods in Enzymology, 70, 3-70, 1980). In this example the labeled analyte can be labeled with either a radioisotope or an enzyme label.

More current immunoassays utilize a double antibody method for detecting the presence of an analyte. These techniques are also reviewed in the above referenced volume of Methods in Enzymology. Therefore, according to one embodiment of the present invention, the presence of the individual markers is determined using a pair of antibodies for each of the markers to be detected. One of said pairs of antibodies is referred to herein as a "detector antibody" and the other of said pair of antibodies is referred to herein as a "capture antibody". One embodiment of the present invention thus uses the double antibody sandwich method for detecting an analyte in a sample of biological fluid. In this method, the analyte is sandwiched between the detector antibody and the capture antibody, the capture antibody being irreversibly immobilized onto a solid support. The detector antibody would contain a detectable label, in order to identify the presence of the antibody-analyte sandwich and thus the presence of the analyte.

Common early forms of solid supports include plates, tubes or beads of polystyrene, all of which are well known in the field of radioimmunoassay and enzyme immunoassay. More recently, a number of porous materials such as nylon, nitrocellulose, cellulose acetate, glass fibers, and other porous polymers have been employed as solid supports.

Various techniques and corresponding sensor devices may be used. Automated assay apparatuses include continuous/random access assay apparatus. Examples of such systems include OPUS™ of PB Diagnostic System, Inc. and the IMX™ Analyzer introduced by Abbott Laboratories of North Chicago, Ill. The automated assay instruments of PB Diagnostic Systems, Inc. are described in U.S. Pat. Nos. 5,051,237; 5,138,868; 5,141,871 and 5,147,609.

Further classes of immunochemical analyzer systems, which can be used in practicing the present invention, are optical immunosensor systems. In general an optical immunosensor is a device that uses optical principles quantitatively to convert chemical or biochemical concentrations or activities of interest into electrical signals. These systems can be grouped into four major categories: reflection techniques; surface plasmon resonance; fiber optic techniques and integrated optic devices. Reflection techniques include ellipsometry, multiple integral reflection spectroscopy, and fluorescent capillary fill devices. Fiber-optic techniques include evanescent field fluorescence, optical fiber capillary tube, and fiber optic fluorescence sensors. Integrated optic devices include planer evanescent field fluorescence, input grading coupler immunosensor, Mach-Zehnder interferometer, Hartman interferometer and difference interferometer sensors. Holographic detection of binding reactions is accomplished detecting the presence of a holographic image that is generated at a predetermined image location when one reactant of a binding pair binds to an immobilized second reactant of the binding pair (see U.S. Pat. No. 5,352,582, issued Oct. 4, 1994 to Lichtenwalter et al.). Examples of optical immunosensors are described in general in a review article by G. A. Robins, Advances in Biosensors 1991, 1:229-256. More specific descriptions of these devices are found for example in U.S. Pat. Nos. 4,810,658; 4,978,503; and 5,186,897; R. A. Brady et al. (Phil. Trans. R. Soc. Land. B. 1987, 316:143-160) and G. A. Robinson et al. (in Sensors and Actuators, Elsevier 1992).

Serological assays are widely used in the determination of influenza diagnosis as well as in research studies regarding the epidemiology and antigenicity of viral strains. In particular, the hemagglutinin inhibition (HI) assay is widely used due to its minimal laboratory requirements and ease of use. It is contemplated that the invention will improve the applicability of the HI assay by increasing its sensitivity. The HI assay may also be used to show the antigenicity of the modified HA molecule, and assist in the characterization of the modified HA molecule as more or less antigenic than non-modified molecules.

The HI assay determines the ability of antibodies from a serum sample to bind with a standardized reference. In the HI assay, serial dilutions (titers) of serum sample are mixed with standard amounts of erythrocytes and their association into complexes is detected visually. The lowest level of titered serum that results in a visible complex is the assay result.

As noted above, the present invention provides for improved production and validation of vaccines for treating or preventing influenza viral infections. In particular, the instant invention is applicable to vaccines made using reverse genetic techniques. It is contemplated that the invention will be of use in the validation and verification of the immune response after vaccination. In particular, but not exclusively, the invention provides for the enhanced detection of antibodies after an individual has been exposed to an influenza virus because of the enhance antigenicity of the modified HA molecule. This enhanced antigenicity is reflected in the increased sensitivity of the assay used to detect the immune response, such as the HI assay.

Vaccine Development

As exemplified below, a modified virus containing an increased antigenicity HA molecule itself is more immunogenic, which in turn provides for a stronger immune response and better vaccine potential.

Strategies to enhance influenza vaccine effectiveness include the use of adjuvants (Wood and Williams, supra), co-administration of immunostimulatory molecules (Salgaller and Lodge, J. Surg. Oncol. 1998, 68:122) and mucosal vaccination strategies. Mucosal immunization strategies include encapsulating the virus in microcapsules (U.S. Pat. No. 5,075,109, U.S. Pat. No. 5,820,883, and U.S. Pat. No. 5,853,763) and using an immunopotentiating membranous carrier (WO 98/0558). In addition, the immunogenicity of orally administered immunogens can be enhanced by using red blood cells (rbc) or rbc ghosts (U.S. Pat. No. 5,643,577), or by using blue tongue antigen (U.S. Pat. No. 5,690,938). Although these approaches are promising for improved future vaccination strategies, their use in specific situations requires validation and surveillance to ensure vaccine effectiveness. It is contemplated that the invention described herein will enhance these strategies including by increasing the ability to detect their immunogenic effects.

EXAMPLES

The following examples illustrate various aspects of the invention, but are not intended to limit it.

Example 1

Serum Antibody Titers of Inoculated Ferrets

Highly pathogenic H5N1 viruses were obtained from World Health Organization (WHO) collaborating laboratories in Asia. All work with these viruses was performed in BL3+ facilities at St. Jude Children's Research Hospital. To compare the immunogenicity of the 2003 influenza viruses of Z genotype, which became dominant in 2004, with that of the 2004 viruses, we inoculated ferrets with the H5N1 virus isolated from a fatal human case (A/HK/213/03) (Guan et al., Proc. Natl. Acad. Sci. USA 2004, 101:8156) and with four H5N1 viruses isolated from humans, chickens, and falcons in 2004 (FIG. 1A). Male and female outbred ferrets were obtained through a special breeding program of the Animal Resources Center at St. Jude Children's Research Hospital. Animals were 3-5 months old and were seronegative by HI tests for exposure to currently circulating influenza A H1N1, H3N2, and H5N1 viruses and influenza B viruses. Viruses were propagated in the allantoic cavities of 10-day-old embryonated chicken eggs at 35° C. for 48 h. Allantoic fluid harvested after a single passage in embryonated chicken eggs was frozen at −80° C. and used in experiments. Serum antibodies were titrated by HI assay with challenge viruses 28 days after inoculation. A/HK/213/03 virus induced high antibody titers (1:640-1:1280), whereas the four 2004 strains induced very low HI titers (1:20-1:40).

The relatively low HI titers to the 2004 H5N1 viruses could have been the result of virus-induced general immune suppression. However, the results of vaccination with ΔH5N1-A/PR/8/34 (6+2) vaccines that included the HA and neuraminidase of A/HK/213/03 and of A/Vietnam/1203/04 indicated that differences in the H5 could be a major contributor to this effect (FIG. 1B). Vaccination with two separate 7 μg doses of ΔH5N1/03 vaccine induced high levels of serum antibodies detectable in both HI and virus neutralization tests (FIG. 1B). After identical vaccination with ΔH5N1/04, very low (approximately 1:20) titers were detected in the HI test, whereas neutralizing titers were much higher (about half that induced by ΔH5N1/03). Previous studies found that inactivated vaccine derived from A/duck/Singapore/3/97 (H5N3) induced little or no detectable serum antibody (Nicholson et al., Lancet 2001, 357:1937; Stephenson et al., Vaccine 2003, 21:1687). Taken together, these results indicate that some H5 isolates may have unusual immunogenic and/or antigenic properties. Alignment of the H5 amino acid sequences revealed that the HAs of A/HK/213/03 and A/Vietnam/1203/04 viruses differ in 10 amino acids in the HA1 region (Table 1b). A/Vietnam/1203/04 virus has a potential glycosylation site at asparagine $N_{154}$ ($N^*_{154}$-$S_{155}$-$T_{156}$, N-X-S/T, X≠P). Sequence comparison revealed three amino acids ($S_{120}$, $K_{189}$, and $S_{223}$) that were present in all of the 2004 viruses but were not present in A/HK/213/03. $K_{212}$ was characteristic for A/Vietnam/1203/04 virus.

Example 2

Generation and Antigenic Characterization of Recombinant ΔH5-A/PR/8/34 Viruses To test the impact of the identified amino acids on immunogenicity and protection against virus challenge, we used the 8-plasmid reverse genetics system to generate recombinant viruses with seven gene segments of A/PR/8/34 and the HA gene segment of A/Vietnam/1203/04 containing single point mutations (Hoffmann et al., Vaccine 2002, 20:3165). Recombinant viruses rendered nonpathogenic by modification of H5 HA at the cleavage site were generated by DNA transfection (Hoffmann et al., Vaccine 2002, 20:3165). Point mutations were inserted into the HA during PCR by using the QuikChange® Site-Directed Mutagenesis Kit (Stratagene, Cedar Creek, Tex., USA) and a set of H5 HA-specific primers. Reassortant viruses contained the HA gene or the HA and neuraminidase (NA) genes from H5N1 viruses in the genetic background of A/PR/8/34 (H1N1) virus (see Table 1a for viruses generated for this study and their abbreviated names). Allantoic fluid harvested after a single passage in embryonated chicken eggs was frozen at −80° C. and used in experiments. The HA genes of the recombinant viruses were amplified by RT-PCR and sequenced to verify that only the designated mutations were present. The amino acid change was verified by sequencing the HA segment of the recombinant viruses (Table 1a).

To evaluate the antigenic properties and diversity of the recombinant HAs, we performed HI assays with a panel of six anti-HA monoclonal antibodies (Table 2). Monoclonal antibodies (mAbs) CP24, CP46, CP58, and 406/7 to the HA of A/chicken/Pennsylvania/1370/83 (H5N3) virus were produced in the Infectious Diseases Department of St. Jude Children's Research Hospital. MAb VN04-6 to the HA of A/Vietnam/1203/04 virus and mAb HK03-3 to the HA of A/HK/213/03 virus were prepared by a modification of the method described by Kohler and Milstein (Kaverin et at, Journal of Virology 2004, 78:240; Kohler et al. European Journal of Immunology 1976, 6:511). Five mAbs reacted at relatively high titers with the ΔH5N1/03 virus, but only 3 reacted with ΔH5/04 HA. The reactivity patterns of $\Delta H5_{S155 \to N, T156 \to A}/04$, $\Delta H5_{S120 \to N}/04$ and $\Delta H5_{R212 \to K}/04$ viruses were similar, in general, to that of ΔH5/04 virus. The reactions of $\Delta H5_{S120 \to N, S155 \to N, T156 \to A}/04$ virus were similar to those of ΔH5N1/03 virus. Four mAbs recognized ΔH5/04 HA with mutation $S_{223} \to N$ ($\Delta H5_{S223 \to N}/04$). The reverse mutation $N_{223} \to S$ in the HA of 2003 virus ($\Delta H5_{N223 \to S}/03$) resulted in significantly decreased HI titers or loss of recognition by mAbs.

Example 3

HI Tests with Chicken and Horse Red Blood Cells

Another interesting observation was obtained in an HI test with chicken and horse red blood cells (RBCs). Interestingly, recombinant $\Delta H5_{S223 \to N}/04$ virus were less able to agglutinate 1% horse RBCs but it agglutinated chicken RBCs to a high titer (1:1024). None of the remaining recombinant viruses differed in their reaction to chicken and horse RBCs to the same extent.

Example 4

Vaccination of Ferrets with H5-Mutant Recombinant Viruses

We assessed the immunogenicity and protective efficacy of the inactivated vaccines by vaccinating groups of 3 ferrets by intramuscular injection with preparations of ΔH5N1/04, ΔH5/04, $\Delta H5_{S155 \to N, T156 \to A}/04$, $\Delta H5_{S120 \to N}/04$, and $\Delta H5_{S223 \to N}/04$ virus standardized for HA content. The single radial immunodiffusion technique was used to standardize ΔH5N1/03 (Webby et al., Lancet 2004, 363:1099). The remaining recombinant viruses were separated by 12% SDS-polyacrylamide gel electrophoresis, the stained gels were analyzed by densitometry on the FUJIFILM Luminescent Image Analyzer LAS-1000plus, and HA was quantified by comparison with a reference protein preparation. After receiving two injections of 7 μg HA, each animal was inoculated with A/Vietnam/1203/04 (H5N1). Groups of 3 ferrets were vaccinated by intramuscular injection of 250 μl sterile PBS containing 7 μg of HA from inactivated purified viruses. Vaccine viruses were inactivated, concentrated, purified as described (Liu et al., Virology 2003, 314:580; Webby et al., Lancet 2004, 363:1099). Three control animals were injected with 250 μl of sterile PBS alone. On day 21 after vaccination, serum was collected and a second intramuscular injection of 7 μg HA was given. Two weeks later, serum was again collected and animals were inoculated with challenge virus.

Figure 2:
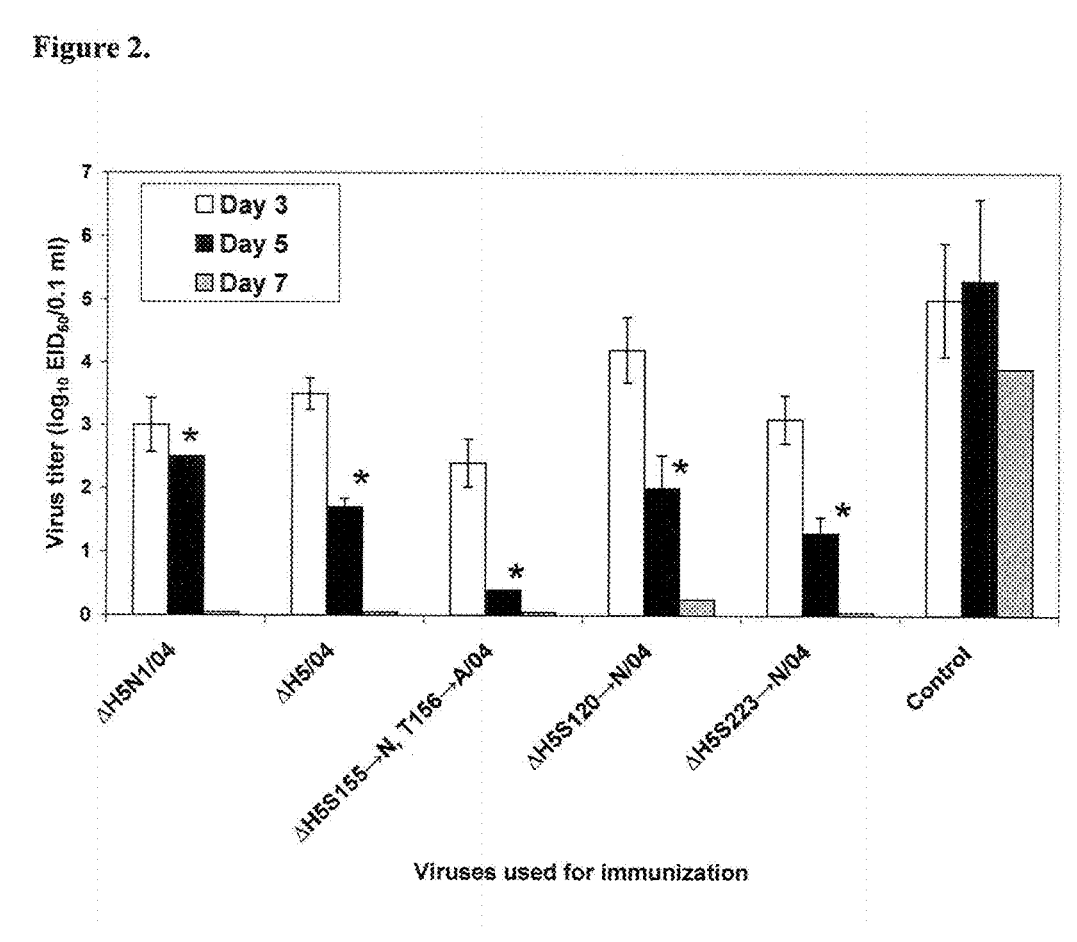

Vaccinated and control animals were inoculated intranasally as previously described with $10^6$ 50% egg infective doses ($EID_{50}$) of A/Vietnam/1203/04 virus (Govorkova et al., Journal of Virology 2005, 79:2191). Clinical signs of infection, body weight, and temperature were monitored daily for two weeks. Ferrets that showed signs of severe disease were sacrificed. To estimate the post-infective immune response, additional groups of ferrets were inoculated with $10^6$ $EID_{50}$ of the human and avian H5N1 isolates A/HK/213/03, A/Vietnam/3046/04, A/Vietnam/3062/04, A/chicken/Vietnam/39/04, and A/falcon/HK/D0028/04. Sera were collected from the animals on day 28 after inoculation. In order to determine virus titers in the upper respiratory tract, specimens were obtained by nasal lavage on days 3, 5, and 7 (Govorkova et al., Journal of Virology 2005, 79:2191). Virus in the samples was titrated in 10-day-old embryonated chicken eggs and expressed as $\log_{10}$ $EID_{50}$ per 0.1 ml. Nasal washes of all vaccinated animals showed virus titers of 2.5-4.5 $\log_{10}$ $EID_{50}$ on day 3, 0.5-2.5 $\log_{10}$ $EID_{50}$ on day 5, and 0.25 $\log_{10}$ $EID_{50}$ or less on day 7 (FIG. 2). Unvaccinated ferrets had a mean titer of 4.0 $\log_{10}$ $EID_{50}$ one week after infection. Two of the 3 control ferrets developed signs of severe disease (massive weight loss and paralysis) and were euthanized, and one died of infection. Only one vaccinated ferret became seriously ill. This ferret, vaccinated with $\Delta H5_{S120 \rightarrow N}/04$ virus, showed severe neurological signs and was euthanized on day 7 after inoculation. This ferret had shown severe viral conjunctivitis on day 4 after inoculation, with subsequent virus spread to the brain. It is likely that virus was transferred to the eyes during the nasal lavage on day 3 and that rapid neuronal spreading to the brain caused encephalitis. The remaining vaccinated ferrets demonstrated decreased activity, loss of body weight, and increased body temperature during the first 3 days after virus challenge. These signs disappeared by day 5 and all animals recovered rapidly. Thus, all vaccine viruses tested protected ferrets from lethal challenge with A/Vietnam/1203/04. Vaccination decreased viral titers in the upper respiratory tract and decreased the duration of virus shedding.

Example 5

HI and Neutralization Tests of the Immunogenicity of Recombinant ΔH5-A/PR/8/34 Viruses Serum from vaccinated ferrets was tested against the recombinant viruses in HI and virus neutralization assays (Tables 3 and 4, respectively). Sera collected from ferrets were treated overnight with *Vibrio cholerae* receptor-destroying enzyme (Denka-Seiken, Tokyo, Japan), heat-inactivated at 56° C. for 30 min, and adsorbed with a 0.5% suspension of chicken erythrocytes (CRBC). Standard HI and virus neutralization tests in MDCK cells were performed as described previously (Palmer et al., US Department of Health, Education and Welfare, Immunology series no. 6. Atlanta: Centers for Disease Control and Prevention. 1975; Kida et al., Virology 1982 122:38).

Four hemagglutinating units (HAU) of virus were used in each HI assay and 100 50% tissue culture infective doses (TCID50) were used in each neutralization assay. Sera from ferrets vaccinated with the wild-type single-gene reassortant virus (ΔH5/04, reference virus) produced HI titers of 1:20. The construct in which the glycosylation site was removed ($\Delta H5_{S155 \rightarrow N; T156 \rightarrow A}/04$) induced HI titers of 1:10-1:20. Mutant ΔH5 $HA_{S120 \rightarrow N}/04$ resulted in HI titers of 1:20 to 1:80. In contrast, vaccination with $\Delta H5_{S223 \rightarrow N}/04$ resulted in an HI titer of 1:640, and the other immune sera tested reacted with $\Delta H5_{S223 \rightarrow N}/04$ virus at high HI titers (1:160 to 1:320). Thus, although the vaccination induced protective immunity, the levels of detectable antibody were different.

All ΔH5/04 viruses produced high titers of virus-neutralizing antibodies after vaccination (1:320 to 1:1280) (Table 4). No substantial differences were observed between homologous and heterologous neutralizing titers. Therefore, the differences observed between the antisera in recognition of the HA did not reflect the ability of the antibodies to neutralize virus.

Example 6

Reactivity of Recombinant Viruses

To further evaluate the reactivity of the recombinant viruses, we used HI assays to test hyperimmune mouse and chicken serum obtained after vaccination with the ΔH5N1/03 and A/HK/213/03 viruses against recombinant viruses with altered HAs (Table 5). The mean HI titers to homologous ΔH5N1/03 virus were 1:2560. HI titers to ΔH5/04 were 1:160. HI titers against recombinant $\Delta H5_{S223 \rightarrow N}/04$ virus were at least twice the titers against the other mutants.

To obtain additional information about the contribution of the amino acid at position 223 to serological reactivity, we generated a recombinant virus in which the H5 was derived from A/HK/213/03, with only the $N_{223} \rightarrow S$ point mutation (Table 1a). This recombinant $\Delta H5_{N223 \rightarrow S}/03$ virus had lower HI titers in chicken and horse RBCs than did the ΔH5N1/03 virus. To further characterize the impact of amino acid 223 on antigen-antibody recognition, we generated recombinant viruses that contained wild-type HA and mutated $S_{223} \rightarrow N$ HA from A/duck/Singapore/3/97 (see Table 1a). These viruses were tested by HI assay against a panel of anti-H5 antisera and mAbs (Table 6). The $S_{223} \rightarrow N$ substitution in the HA dramatically increased the HI titers (by a factor of 4 or more). However, this mutation did not significantly alter the reactivity pattern of A/duck/Singapore/3/97 HA, especially in the reactions with mAbs: neither the original nor the mutant HA reacted with mAbs HK03-3 and CP46, and both reacted at a low titer with CP46 (Table 6). These results demonstrate that the $S_{223} \rightarrow N$ substitution in HA increases the sensitivity of the HI assay.

Example 7

Second Generation Diagnostic Reference Viruses that are Predicted to Increase the Sensitivity of the HI Assay We have previously demonstrated in Example 3 above that by converting the amino acid at position 223 of H5 HA to asparagine the sensitivity of the HI test using chicken red blood cells was increased. We have provided evidence that the molecular basis of this effect was caused by an altered receptor specificity. The mutant virus with increased sensitivity did not agglutinate horse red blood cells which have only alpha 2,3 linkage. Thus, amino acid changes that result in the inability to agglutinate horse red blood cells are candidates with increased sensitivity potential in the HI assay using chicken red blood cells. This concept can be applied to all 16 HA subtypes, especially avian influenza A viruses which have 2,3 specificity.

Reverse genetics techniques allow for the generation of recombinant viruses which have minor changes in their antigenic structures but are 'optimized' in recognition of different cell substrates. Preferably amino acids (91, 130-134, 149, 151, 179, 186, 190-191, 220-225 for H5) are mutated that are close to or part of the receptor binding site. Plasmids with genetically engineered HAs may be constructed and viruses may be generated by cotransfection. The recombinant viruses may be tested by HA assays using chicken red blood cells and horse red blood cells in parallel. Candidate viruses that do agglutinate chicken red blood cells but do not agglutinate horse red blood cells will be candidates for testing in HI tests. In complementary experiments viruses are generated that agglutinate horse red blood cells but do not agglutinate chicken red blood cells The combination of candidates with single amino changes may increase the sensitivity further. It is expected that the evaluation of the candidates will lead to diagnostic reference viruses with specific reactivity to receptors with 2,3 specificity.

TABLE 1b

Sequence differences in the HA1 protein of H5N1 influenza viruses.

| | Amino acid position in HA1 | | | | | | | | | |
|---|---|---|---|---|---|---|---|---|---|---|
| Virus | 36 | 83 | 86 | 120 | 155 | 156 | 189 | 212 | 223 | 263 |
| A/HK/213/03 | T | A | A | N | N | A | R | K | N | A |
| A/Vietnam/1203/04 | K | T | V | S | S | T | K | R | S | T |
| A/Vietnam/3046/04 | T | A | V | S | S | T | K | R | S | T |
| A/Vietnam/3062/04 | T | A | V | S | S | T | K | R | S | T |
| A/chicken/Vietnam/39/04 | T | A | V | S | S | T | K | R | S | T |
| A/falcon/HK-D0028/04 | T | A | A | S | S | A | K | K | S | A |
| A/duck/Singapore/3/97 | T | D | V | S | N | A | K | E | S | A |
| A/HK/156/97 | T | A | A | S | S | A | K | E | S | T |

TABLE 2

HI analysis of ΔH5 recombinant viruses with anti-H5 monoclonal antibodies

| | Monoclonal antibodies to H5 (HI titers) | | | | | |
|---|---|---|---|---|---|---|
| Virus | VN04-6* | HK03-3† | CP24‡ | CP46‡ | CP58‡ | 406/7‡ |
| ΔH5N1/03 | 51200 | 6400 | 1600 | 100 | 1600 | 800 |
| ΔH5/04 | 12800 | <100 | 800 | <100 | 1600 | <100 |
| ΔH5$_{S155 \to N, T156 \to A}$/04 | 3200 | <100 | 800 | <100 | 800 | 100 |
| ΔH5$_{S120 \to N}$/04 | 12800 | 200 | 800 | <100 | 1600 | <100 |
| ΔH5$_{R212 \to K}$/04 | 12800 | 100 | 1600 | <100 | 6400 | <100 |
| ΔH5$_{S223 \to N}$/04 | 51200 | 3200 | 12800 | <100 | 25600 | <100 |
| Δ115$_{S120 \to N, S155 \to N, T156 \to A}$/04 | 12800 | 1600 | 3200 | <100 | 1600 | 200 |
| ΔH5$_{N223 \to S}$/03 | 12800 | 800 | ≤100 | <100 | 200 | <100 |

HI tests were performed in microtiter plates with 0.5% chicken RBCs. Titers are the reciprocal lowest dilutions of mAbs that inhibited hemagglutinin caused by 4 hemagglutinating units (HAU) of virus.
*anti-HA mAb to A/Vietnam/1203/04 virus;
†anti-HA mAb to A/HK/213/03 virus;
‡anti-HA mAb to A/chicken/Pennsylvania/1370/83 virus.

TABLE 1a

Recombinant H5-PR/8/34 viruses generated for use in this study.

| Recombinant virus: | | Amino acid position in HA1 | | | | | | | | | |
|---|---|---|---|---|---|---|---|---|---|---|---|
| Full name | Abbreviation* | 36 | 83 | 86 | 120 | 155 | 156 | 189 | 212 | 223 | 263 |
| A/HK/213/03 ΔH5N1 × PR/8/34 | ΔH5N1/03 | T | A | A | N | N | A | R | K | N | A |
| A/Vietnam/1203/04 ΔH5N1 × PR/8/34 | ΔH5N1/04 | K | T | V | S | S | T | K | R | S | T |
| A/Vietnam/1203/04 ΔH5 × PR/8/34 | ΔH5/04 | K | T | V | S | S | T | K | R | S | T |
| A/Vietnam/1203/04 ΔH5$_{S155 \to N, T156 \to A}$ × PR/8/34 | ΔH5$_{S155 \to N, T156 \to A}$/04 | T | A | V | S | N | A | K | R | S | T |
| A/Vietnam/1203/04 ΔH5$_{S120 \to N}$ × PR/8/34 | ΔH5$_{S120 \to N}$/04 | T | A | V | N | S | T | K | R | S | T |
| A/Vietnam/1203/04 ΔH5$_{R212 \to K}$ × PR/8/34 | ΔH5$_{R212 \to K}$/04 | T | A | V | S | S | T | K | K | S | T |
| A/Vietnam/1203/04 ΔH5$_{S223 \to N}$ × PR/8/34 | ΔH5$_{S223 \to N}$/04 | T | A | A | S | S | T | K | R | N | A |
| A/Vietnam/1203/04 ΔH5$_{S120 \to N, S155 \to N, T156 \to A}$ × PR/8/34 | ΔH5$_{S120 \to N, S155 \to N, T156 \to A}$/04 | T | A | A | N | N | A | K | R | N | A |
| A/HK/213/03 ΔH5$_{N223 \to S}$ × PR/8/34 | ΔH5$_{N223 \to S}$/03 | T | A | A | N | N | A | R | K | S | A |
| A/duck/Singapore/3/97 H5 × PR/8/34 | H5/97† | T | D | V | S | N | A | K | E | S | A |
| A/duck/Singapore/3/97 H5$_{S223 \to N}$ × PR/8/34 | H5$_{S223 \to N}$/97 | T | D | V | S | N | A | K | E | N | A |

*A multibasic amino acids in the H5 were removed by genetic engineering.
†Wild-type A/duck/Singapore/3/97 does not have multibasic amino acids.

TABLE 3

Immunogenicity of A/Vietnam/1203/04 ΔH5 HA recombinant viruses in ferrets.

HI titer of sera after immunization with:

| Virus | ΔH5/04 | | | ΔH5$_{S155 \to N, T156 \to A}$/04 | | | ΔH5$_{S120 \to N}$/04 | | | ΔH5$_{S223 \to N}$/04 | | |
|---|---|---|---|---|---|---|---|---|---|---|---|---|
| ΔH5N1/03 | 20 | 20 | 10 | 160 | 80 | 160 | 20 | 20 | 10 | 20 | 10 | 10 |
| ΔH5/04 | <u>20</u> | <u>20</u> | <u>20</u> | 20 | 20 | 20 | 20 | 20 | 20 | 20 | 20 | 20 |
| ΔH5$_{S155 \to N, T156 \to A}$/04 | | | | <u>20</u> | <u>10</u> | <u>20</u> | | | | | | |
| ΔH5$_{S120 \to N}$/04 | | | | | | | <u>80</u> | <u>80</u> | <u>20</u> | | | |
| ΔH5$_{S223 \to N}$/04 | 160 | 320 | 320 | 160 | 320 | 160 | 320 | 320 | 320 | <u>640</u> | <u>640</u> | <u>640</u> |

Eleven-week-old influenza-seronegative ferrets were vaccinated twice at 3-week intervals by intramuscular injection of inactivated, purified and concentrated virus preparation containing 7 μg HA in 250 μl of PBS. Data are the HI titers from 3 ferrets presented individually. HI tests used 0.5% chicken RBCs.

TABLE 4

Virus-neutralization titers of ferret sera after vaccination with viruses containing the modified HA of A/Vietnam/1203/04 virus.

Neutralizing antibody titers after immunization with:

| Virus | ΔH5N1/04 | | | ΔH5/04 | | | ΔH5$_{S155 \to N, T156 \to A}$/04 | | | ΔH5$_{S223 \to N}$/04 | | | mock |
|---|---|---|---|---|---|---|---|---|---|---|---|---|---|
| ΔH5N1/03 | 1280 | 1280 | 320 | 640 | 320 | 640 | 1280 | 1280 | 320 | 640 | 640 | 640 | <80 |
| ΔH5N1/04 | <u>2560</u> | <u>1280</u> | <u>640</u> | 1280 | 640 | 640 | 1280 | 1280 | 640 | 640 | 1280 | 1280 | <80 |
| ΔH5/04 | 1280 | 1280 | 640 | <u>1280</u> | <u>640</u> | <u>640</u> | 1280 | 1280 | 640 | 640 | 1280 | 1280 | <80 |
| ΔH5$_{S155 \to N, T156 \to A}$/04 | 1280 | 1280 | 640 | 1280 | 640 | 640 | <u>1280</u> | <u>1280</u> | <u>640</u> | 1280 | 1280 | 1280 | <80 |
| ΔH5$_{S223 \to N}$/04 | 1280 | 1280 | 1280 | 1280 | 1280 | 640 | 1280 | 1280 | 320 | <u>1280</u> | <u>1280</u> | <u>1280</u> | <80 |
| ΔH5$_{S223 \to N}$N1/04 | 1280 | 1280 | 640 | 1280 | 640 | 640 | 1280 | 1280 | 640 | 1280 | 1280 | 1280 | <80 |

5 Neutralization assay was performed in MDCK cells. Titers are the reciprocal lowest dilutions of sera that completely inhibited 100 TCID$_{50}$ of virus. Homologous titers are underlined. Values are the neutralizing titers from 3 ferrets presented individually.

TABLE 5

HI testing of antisera to 2003 H5N1 against mutant viruses

| | Polyclonal antiserum to: | |
|---|---|---|
| Virus | vaccine ΔH5N1/03 | A/HK/213/03 (H5N1) |
| ΔH5N1/03 | 2560 | 2560 |
| ΔH5/04 | 160 | 160 |
| ΔH5$_{S155 \to N; T156 \to A}$ | 80 | 320 |
| ΔH5$_{S120 \to N}$/04 | 320 | 320 |
| ΔH5$_{S223 \to N}$/04 | 1280 | 640 |

HI test was performed in microtiter plates with 0.5% chicken RBCs (Palmer et al., in US Department of Health, Education and Welfare, Immunology series no. 6. Atlanta: Centers for Disease Control and Prevention, 1975). Titers are the reciprocal lowest dilutions of sera that inhibited hemagglutinin caused by 4 HAU of virus.

TABLE 6

Antigenic analysis of H5/97 and H5$_{S223 \to N}$/97 viruses with polyclonal and monoclonal antibodies.

| | HI titer of polyclonal antisera: | | | | | | HI titer of mABs: | | | | | |
|---|---|---|---|---|---|---|---|---|---|---|---|---|
| Virus | A/ck/Hid algo/94 | A/HK/15 6/97 | A/Gs/HK /497-4/97 | A/ck/HK/ YU22/02 | A/HK/21 3/03 | ΔH5/03 | VN04-6* | HK03-3[†] | CP58[‡] | CP24[‡] | CP46[‡] | CP406/7[‡] |
| ΔH5/03 | 20 | 320 | 5120 | 12 800 | 160 | 5 120 | 25 600 | 6 400 | 1 600 | 12 800 | <100 | 1 600 |
| H5/97 | 40 | 640 | 640 | 320 | <10 | 10 | 3 200 | <100 | 3 200 | 1 600 | <100 | 3 200 |
| H5$_{S223 \to N}$/97 | 320 | 10 240 | 10 240 | 2 560 | 80 | 1 280 | 25 600 | <100 | 25 600 | 51 200 | 200 | 25 600 |

*anti-HA mAb to A/Vietnam/1203/04 virus;
[†]anti-HA mAb to A/HK/213/03 virus;
[‡]anti-HA mAb to A/chicken/Pennsylvania/1370/83 virus.

HI test was performed in microtiter plates with 0.5% chicken RBCs (14). Titers are the reciprocal lowest dilutions of sera that inhibited hemagglutinin caused by 4 HAU of virus.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

All patents and patent applications cited herein are hereby incorporated herein by reference in their entireties.

What is claimed is:

1. An immunogenic composition comprising
   (a) a recombinant influenza virus H5 hemagglutinin (HA) molecule, wherein said recombinant H5 HA molecule:
      (i) comprises one or more amino acid sequence changes as compared to a naturally occurring HA molecule that comprises an amino acid other than asparagine at an amino acid position corresponding to amino acid position 223 in H5 HA;
      (ii) comprises an asparagine at an amino acid position corresponding to amino acid position 223 in H5 HA;
      (iii) has an increased reactivity with antisera derived from an animal exposed to an H5 influenza virus or an H5 influenza vaccine as compared to said naturally occurring HA molecule; and
      (iv) is not A/HK/213/03 HA molecule, and
   (b) a carrier.

2. The immunogenic composition of claim 1, wherein the carrier comprises an adjuvant.

3. The immunogenic composition of claim 1, wherein the immunogenic composition further comprises an immunostimulatory molecule.

4. The immunogenic composition of claim 1, wherein the immunogenic composition further comprises microcapsules and/or an immunopotentiating membranous carrier.

5. The immunogenic composition of claim 1, wherein the immunogenic composition further comprises red blood cells (rbc), rbc ghosts, or blue tongue antigen.

6. The immunogenic composition of claim 1, wherein the immunogenic composition is administrable intramuscularly.

7. The immunogenic composition of claim 1, wherein the immunogenic composition is administrable orally.

8. The immunogenic composition of claim 1, wherein the immunogenic composition is administrable mucosally.

9. The immunogenic composition of claim 1, wherein the one or more amino acid sequence changes alter a glycosylation site.

10. The immunogenic composition of claim 1, wherein said naturally occurring HA molecule is from a human influenza A virus.

11. The immunogenic composition of claim 10, wherein the human influenza A virus is a member of the H5 subtype.

12. The immunogenic composition of claim 1, wherein said naturally occurring HA molecule is from an avian influenza virus.

13. The immunogenic composition of claim 1, wherein the asparagine at amino acid position 223 of the HA molecule alters specificity for sialic acid receptors.

14. The immunogenic composition of claim 1, wherein the HA molecule is part of a recombinant or attenuated virus.

15. An immunogenic composition comprising
   (a) a recombinant influenza virus comprising a recombinant influenza virus H5 hemagglutinin (HA) molecule, wherein said recombinant H5 HA molecule:
      (i) comprises one or more amino acid sequence changes as compared to a naturally occurring HA molecule that comprises an amino acid other than asparagine at an amino acid position corresponding to amino acid position 223 in H5 HA;
      (ii) comprises an asparagine at an amino acid position corresponding to amino acid position 223 in H5 HA;
      (iii) has an increased reactivity with antisera derived from an animal exposed to an H5 influenza virus or an H5 influenza vaccine as compared to said naturally occurring HA molecule; and
      (iv) is not A/HK/213/03 HA molecule, and
   (b) a carrier.

16. The immunogenic composition of claim 15, wherein the one or more amino acid sequence changes alter a glycosylation site.

17. The immunogenic composition of claim 15, wherein said naturally occurring HA molecule is from a human influenza A virus.

18. The immunogenic composition of claim 17, wherein the human influenza A virus is a member of the H5 subtype.

19. The immunogenic composition of claim 15, wherein said naturally occurring HA molecule is from an avian influenza virus.

20. The immunogenic composition of claim 15, wherein the asparagine at amino acid position 223 of the HA molecule alters specificity for sialic acid receptors.

* * * * *